United States Patent [19]
Pinza et al.

[11] Patent Number: 4,703,054
[45] Date of Patent: Oct. 27, 1987

[54] NOOTROPIC IMIDAZOLIDINONES

[75] Inventors: Mario Pinza, Milan; Carlo Farina, Como; Silvano Banfi; Ugo Pfeiffer, both of Milan, all of Italy

[73] Assignee: ISF, S.p.A., Milan, Italy

[21] Appl. No.: 876,946

[22] Filed: Jun. 20, 1986

[30] Foreign Application Priority Data

Jun. 21, 1985 [IT] Italy ................. 21236 A/85

[51] Int. Cl.⁴ .................. A61K 31/415; C07D 233/38
[52] U.S. Cl. ..................................... 514/386; 548/301
[58] Field of Search ................... 548/301; 514/386

[56] References Cited

U.S. PATENT DOCUMENTS 3,428,646  2/1969  Hellerbach .................. 548/301

OTHER PUBLICATIONS

V. Klixkull et al, Int'l. J. of Pharm., 20, 273–284 (1984).
Chem. Abstracts, 94, 121894u (1981).
Chem. Abstracts, 63, 2978h (1965).
P. Hardy, et al., J. Chem. Soc. Perkin I, 1954–1960 (1977).
Y. Ariyoshi, et al., Bull. Chem. Soc. Japan, 45, 2015–2018 (1972).
C. Panetta, et al., J. Org. Chem., 37, 302–304 (1972).
F. Cardinaux, et al., Helv. Chim. Acta, 56, 339–347 (1973).

Primary Examiner—Richard A. Schwartz
Attorney, Agent, or Firm—Nancy S. Mayer; Stuart R. Suter; Alan D. Lourie

[57] ABSTRACT

The invention relates to 4-imidazolidinone derivatives which help restore learning and memory difficulties associated with ageing. A compound of the invention is 1-(2-aminoacetyl)-2,2-dimethyl-4-imidazolidinone, of the formula:

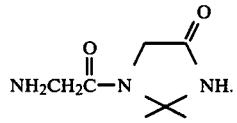

12 Claims, No Drawings

NOOTROPIC IMIDAZOLIDINONES

This invention relates to new chemical compounds which have useful pharmacological activity, to processes and intermediates for making them, and pharmaceutical compositions containing them.

According to the invention we provide compounds of Structure (1):

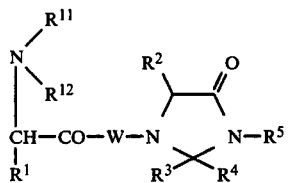

in which $R^1$ is H, $C_{1-5}$alkyl (straight or branched), or phenyl;

W is a bond, —NHCHR$^6$CO— or —NHCHR$^6$CONHCHR$^7$CO—, where $R^6$ and $R^7$, which can be the same or different are H or $C_{1-5}$alkyl (straight or branched);

$R^2$ is H, $C_{1-5}$alkyl (straight or branched), aryl or a benzyl group optionally substituted by $C_{1-5}$ alkyl (straight or branched), $C_{1-4}$ alkoxy (straight or branched) or hydroxy;

$R^3$ and $R^4$, which can be the same or different, are H, $C_{1-5}$alkyl (straight or branched) or phenyl, or $R^3$ and $R^4$ are taken together to form a 1,4-butylene or 1,5-pentylene group;

$R^5$ is H or —CHR$^8$CONR$^9$R$^{10}$, where $R^8$, $R^9$ and $R^{10}$, which can be the same or different, are H or $C_{1-5}$alkyl (straight or branched);

$R^{11}$ and $R^{12}$, which can be the same or different, are H, $C_{1-5}$alkyl (straight or branched), or acyl or taken together with the nitrogen atom shown to form a 2-oxo-pyrrolidino group optionally substituted in the 4-position by a hydroxy or $C_{1-5}$ alkoxy (straight or branched) group, or a 5-oxo-1-imidazolidine group optionally substituted at the 2-position by one or two $C_{1-5}$ alkyl (straight or branched) groups or a 1,4-butylene or 1,5-pentylene group, or optionally substituted at the 4-position by $C_{1-5}$ alkyl, and pharmaceutically acceptable salts thereof.

Preferably $R^1$ is H, methyl or isobutyl, particularly H. Preferably $R^2$ is H or methyl. For $R^2$ examples of aryl groups are phenyl and naphthyl, which may be optionally substituted by $C_{1-5}$alkyl (straight or branched), $C_{1-4}$alkoxy (straight or branched) or hydroxy. Preferably the aryl groups are phenyl, 4-hydroxyphenyl and 4-methoxyphenyl.

For $R^{11}$ and $R^{12}$ examples of acyl groups are $C_{1-5}$ alkanoyl (straight or branched) groups, particularly formyl, acetyl and propionyl, and aroyl groups, particularly benzoyl and substituted benzoyl groups such as 4-methoxybenzoyl.

Preferably $R^3$ and $R^4$ are both methyl or taken together to form a 1,4-butylene or 1,5-pentylene group, or $R^3$ is isopropyl and $R^4$ is hydrogen.

Preferably $R^5$ is H or $CH_2CONH_2$.

Preferably $R^8$ is H, methyl, isopropyl, 1-methylpropyl or isobutyl, particularly H.

Preferably $R^9$ is H, methyl, isopropyl, 1-methylpropyl or isobutyl, particularly H.

Preferably $R^{10}$ is H, methyl, isopropyl, 1-methylpropyl or isobutyl, particularly H.

Preferred compounds of the present invention are:
1-(2-aminoacetyl)-2,2-dimethyl-4-imidazolidinone,
1-(2-aminoacetyl)-2-isopropyl-4-imidazolidinone,
1-(2-aminopropanoyl)-2,2-dimethyl-4-imidazolidinone,
1-(2-benzylaminoacetyl)-2,2-dimethyl-4-imidazolidinone,
3-(2-aminoacetyl)-2,2-dimethyl-5-oxo-1-imidazolidine acetamide,
2,2-dimethyl-1-(2-oxo-1-pyrrolidineacetyl)-4-imidazolidinone,
2,2-dimethyl-5-oxo-3-(2-oxo-1-pyrrolidineacetyl)-1-imidazolidineacetamide,
2,2-dimethyl-1-[2-(2-oxo-1-pyrrolidineacetamido)-acetyl]-4-imidazolidinone,
2,2-dimethyl-1-(4-hydroxy-2-oxo-1-pyrrolidineacetyl)-4-imidazolidinone,
2,2-dimethyl-5-oxo-3-(4-hydroxy-2-oxo-1-pyrrolidineacetyl)-1-imidazolidineacetamide,
2,2-dimethyl-1-[2-(4-hydroxy-2-oxo-1-pyrrolidineacetamido)acetyl]-4-imidazolidinone,
2-isopropyl-1-pyrrolidineacetyl-4- imidazolidinone,
4-(4-hydroxy-2-oxo-1-pyrrolidineacetyl)-1,4-diazaspiro-[4,5]-decan-2-one,
1-[2-[2-(2-aminoacetamido)acetamido]acetyl]-2,2-dimethyl]-4-imidazolidinone,
2,2-dimethyl-1-[2-(2-isopropyl-5-oxo-1-imidazolidineacetamido)acetyl]-4-imidazolidinone,
2,2-dimethyl-1-[2-(2,2-dimethyl-5-oxo-1-imidazolidineacetamido)acetyl]-4-imidazolidinone,
1-(2-aminoacetyl)-2,2,5-trimethyl-4-imidazolidinone,
1-(2-aminoacetyl)-2-isopropyl-5-methyl-4-imidazolidinone,
1-[2-(2S-amino-4-methylpentanamido)acetyl]-2,2-dimethyl-4-imidazolidinone,
1-(2-acetamidoacetyl)-2,2-dimethyl-4-imidazolidinone,
3-(2-aminopropionyl)-2,2-dimethyl-5-oxo-1-imidazolidineacetamide,
3-(2-aminoacetyl)-2-isopropyl-5-oxo-1-imidazolidineacetamide,
3-(2-aminoacetyl)-2,2,4-trimethyl-5-oxo-1-imidazolidineacetamide,
3-(2-acetamidoacetyl)-2,2-dimethyl-5-oxo-1-imidazolidineacetamide,
2-isopropyl-1-[2-(2-oxo-1-pyrrolidineacetamido)acetyl]-4-imidazolidinone,
2,2-dimethyl-1-[2-(2-oxo-1-pyrrolidineacetamido)propionyl]-4-imidazolidinone,
2,2-dimethyl-1-(4-hydroxy-2-oxo-1-pyrrolidineacetyl)-4-imidazolidinone,
1-[2-(2-oxo-1-pyrrolidineacetamido)acetyl]-2,2,5-trimethyl-4-imidazolidinone,
2-isopropyl-5-methyl-1-[2-(2-oxo-1-pyrrolidineacetamido)-acetyl]-4-imidazolidinone,
2,2-dimethyl-1-[2-(2,2-dimethyl-4-isobutyl-5-oxo-1-imidazolidine)acetyl]-4-imidazolidinone, and
1-[2-(4-hydroxy-2-oxo-1-pyrrolidineacetamido)acetyl]-2,2,5-trimethyl-4-imidazolidinone,
and their pharmaceutically acceptable salts.

It will be appreciated that there will be chiral centres present if $R^1$ is other than hydrogen, if $R^3$ and $R^4$ are different, and if any of $R^5$, $R^6$, $R^7$ and $R^8$ are other than hydrogen. The present invention includes all optical isomers of the compounds of Structure (1) in their resolved and partially resolved forms and in the forms of racemic mixtures. When the synthetic precursor for the substituent can be a natural aminoacid then preferably that substituent will have the natural (L) configuration.

The compounds of Structure (1) can be prepared by the following general methods:

(A) by reacting a carboxylic acid of Structure (2) with an imidazolidinone compound of Structure (3).

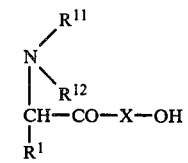
(2)

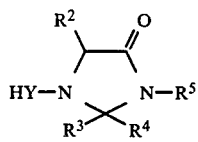
(3)

In structures (2) and (3) $R^1$, $R^2$, $R^3$, $R^4$, $R^5$, $R^{11}$ and $R^{12}$ are as defined for Structure (1), and X and Y are each a bond, —NHCHR$^6$CO— or —NHCHR$^6$CONHCHR$^7$CO— (where $R^6$ and $R^7$, which can be the same or different are H or $C_{1-5}$ alkyl (straight or branched)) provided that X and Y combined are a bond, —NHCHR$^6$CO— or —NHCHR$^6$CONHCHR$^7$CO—.

This reaction will require activation of the carboxyl group or the use of a peptide coupling reagent. The use of either procedure might necessitate the temporary protection of any hydroxy groups present and any amino groups which are not involved in the reaction.

Preferably this reaction is carried out in an aprotic solvent, for example a chlorinated hydrocarbon, e.g. 1,2-dichloroethane, or in a dipolar aprotic solvent such as tetrahydrofuran, dioxane, dimethylformamide, dimethylacetamide, dimethyl sulphoxide or hexamethylphosphoramide.

For reactions in which Y is a bond in the compounds of Structure (3) the amine is a secondary amine and may be sterically hindered, and preferably a peptide coupling reagent or an acid azide or mixed anhydride is used rather than an activated ester.

(B) For those compounds of Structure (1) in which $R^{11}$ and $R^{12}$ are hydrogen or $C_{1-5}$ alkyl, by reacting a compound of Structure (4), in which W, $R^1$, $R^2$, $R^3$, $R^4$ and $R^5$ are as defined for Structure (1) and Z is a leaving group displaceable with an amine, with an amine $HNR^{11}R^{12}$ (in which $R^{11}$ and $R^{12}$ are hydrogen or $C_{1-5}$ alkyl).

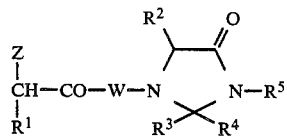
(4)

Examples of leaving groups displaceable with an amine are chlorine, bromine, alkylsulphonyloxy (e.g. methanesulphonyloxy) or arylsulphonyloxy (e.g. p-toluenesulphonyloxy). The compounds of Structure (4) can be prepared by reacting a compound of Structure (3) with a compound of structure ZCHR$^1$COX, in which Z and $R^1$ are as described for Structure (4) and X is a leaving group, for example chloroacetyl chloride, or bromoacetyl bromide.

(C) For those compounds of Structure (1) in which $R^{11}$ and $R^{12}$ together with the nitrogen atom shown form a 2-oxopyrrolidine group optionally substituted by a 4-hydroxy group, by reacting a compound of Structure (5) with 4-chlorobutyryl chloride or a 3,4-epoxybutanoate ester. When the 2-oxopyrrolidine group is not substituted, 4-chlorobutyryl chloride is used and preferably, the reaction and subsequent cyclisation is carried out in the presence of a base such as sodium ethoxide or anion exchange resin. When the 2-oxopyrrolidine group is 4-hydroxy substituted, a 3,4-epoxybutanoate ester is used and the amine group in Structure (5) may necessitate protection. If an amine protecting group, for example a benzyl group is used, then it must be removed before subsequent thermal cyclisation. Suitable protection and deprotection methods will be apparent to those skilled in the art.

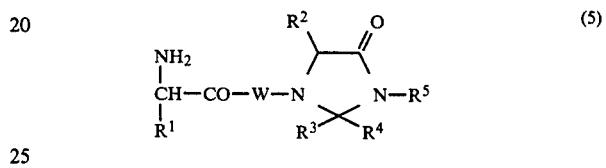
(5)

The intermediates of Structure (3) in which Y is other than a bond can be prepared by reacting a compound of Structure (3) in which Y is a bond with an amino-protected derivative of an aminoacid or a dipeptide and subsequent removal of the amino-protecting group. This procedure will necessitate the activation of the carboxyl group or the use of a peptide coupling agent. The intermediates of Structure (3) in which HY is $NH_2CH_2CO$— can also be prepared by successive reaction of a compound of Structure (3) in which Y is a bond with chloroacetyl chloride or bromoacetyl bromide and ammonia. The intermediates of Structure (3) in which Y is a bond and $R^5$ is $CHR^8 CONR^9R^{10}$ can be prepared by reacting carboxylic acids (described by Panetta et al. J. Org. Chem., 37, 302, 1972) with thionyl chloride and an alkanol followed by treatment with an amine, and by processes analogous to those described by Panetta et al. The intermediates of structure (3) in which Y is a bond and $R^5$ is H can be prepared according to the literature (see for example: A. C. Davis et al., J. Chem. Soc., 1951,3479; U. Zehavi et al., J. Org. Chem., 26, 1097, 1961; P. G. Wiering et al., Rec. Trav. Chim. Pays-Bas, 111, 284, 1971; T. Toda et al., Bull. Chem. Soc. Jap., 44, 3445, 1971; T. Polonski, Tetrahedron, 41, 611, 1985).

(D) For compounds of Structure (1) in which $R^{11}$ and $R^{12}$ together with the nitrogen atom form an optionally substituted 5-oxo-1-imidazolidine group by reacting a compound of Structure (6):

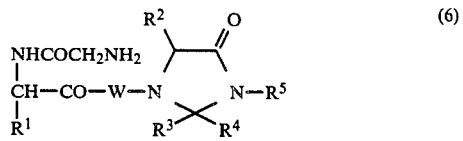
(6)

in which $R^1$, $R^2$, $R^3$, $R^4$, $R^5$ and W are as defined for Structure (1), with an aldehyde or ketone. When the carbonyl compound is an aldehyde, from equimolar to two molar equivalents of aldehyde are used. When the carbonyl compound is a ketone preferably a larger excess of the ketone is used, together with higher temperatures and/or longer reaction times than for the corresponding reactions with aldehydes. Suitable aldehydes and ketones include, for example compounds of Structure $R_2CO$, in which each group R is hydrogen or $C_{1-5}$ alkyl, or taken together the two groups R form a 1,4-butylene or 1,5-pentylene group.

Suitable methods for activating carboxyl groups, suitable peptide coupling reagents and protecting groups are all well known to the art and are described for example in 'Peptide Synthesis' by M. Bodansky, Y. Klausner and M. Ondetti (Wiley 1976) and in 'Protective Groups in Organic Synthesis' by T. W. Greene (Wiley, 1981). Examples of activated derivatives of carboxyl groups are acyl chlorides, acyl azides, mixed anhydrides (e.g. formed with an alkyl chloroformate or pivaloyl chloride) and activated esters (e.g. trichlorophenyl, N-hydroxysuccinimido and 1-hydroxybenzotriazole esters). Examples of peptide coupling reagents are carbodiimides and Woodward's Reagent K (N-ethyl-5-phenylisoxazolium-3'-sulphonate). Examples of nitrogen-protecting groups are benzyloxycarbonyl and t-butyloxycarbonyl.

When the peptide side chain contains chiral centres (i.e. when $R^6$ and $R^7$ are other than hydrogen) then the route of synthesis and the reagents will be chosen to ensure that only a small degree of racemisation occurs under the reaction conditions.

The compounds of Structure (1) have useful nootropic activity that is they help restore learning and memory difficulties associated with ageing and various pathologies including Alzheimer's disease. The present invention therefore provides, in a further aspect a method of restoring learning and treating memory difficulties which comprises administering to a mammal in need thereof a non-toxic effective amount of a compound of Structure (1). To evaluate the nootropic activity, the compounds were submitted to pharmacological tests designed to detect a positive action on cognitive processes disrupted by an experimental cerebral impairment. In particular the protection against the amnesia induced by maximal electroconvulsive shock (ECS) was considered. The experimental procedure described by Banfi et al. (J. Pharmacol Methods, 8, 255–264, 1982) was followed.

Male albino CD Swiss mice from Charles River (Calco, Italy) are used. Mice were 35 days old. The apparatus is essentially the same as described by Essman [Pharm. Res. Commun., 5, 295–302, 1973]. The passage from a light box (10×10×12 cm) into a dark one (23×16×12 cm) was punished by unavoidable foot shocks (0.3 mA, 50 Hz, 5 sec). In order to erase newly encoded information in the memory, a maximal ECS (30 mA, 150 msec, 50 Hz) is given to the mice by corneal electrodes immediately after the trial. The retest is performed 24 hr after ECS. Mice that did not cross from the light box into the dark one in 60 sec were considered as not affected by the retrograde amnesic effect of ECS. Groups of control animals were submitted to sham ECS to demonstrate the amnesic action of ECS. Saline or tested compounds are injected i.p. to groups of at least 20 mice 1 hr before the conditioning trial. The number of animals showing retention over the total number in each treated group is compared with that of controls by the chi square test.

The compounds under study are tested at the doses of 0.3 mg/kg, 1 mg/kg, 10 mg/kg and 30 mg/kg. The difference in percentage retention between the control saline-treated mice submitted to ECS and those submitted to sham ECS demonstrated the amnesic action of ECS. The degree of protective activity of the compounds is evaluated by comparing the groups treated with the compounds plus ECS to the group treated with saline alone plus ECS. Significant protective action can be observed, for example, after intraperitoneal administration of 3-(2-aminoacetyl)-2,2-dimethyl-5-oxo-imidazolidine-1-acetamide hydrochloride or 2,2-dimethyl-1-[2-(2-oxo-1-pyrrolidineacetamido)acetyl]-4-imidazolidinone in a dose range from 0.3 to 30 mg/kg.

The specific mechanism of action of the compounds can be characterised by high affinity choline uptake determinations using synaptosomal preparations from cortical and hippocampal rat tissues, for example as described by F. Pedata et al. Clinical Neuropharmacology 7 (Suppl. 1) 772–3 (1984). Activity in this test indicates that the compounds might enhance cholinergic neurotransmission by increasing the amount of choline pre-synaptically available which in turn would lead to an increase in brain acetylcholine levels, thus improving the performance of brains in which choline and acetylcholine levels were abnormally low.

An alternative method for investigating the selective action of the compounds of structure (1) is to test their activity in rats against both the disruptive action of scopolamine on mnestic trace and on the reduction of acetylcholine levels in hippocampus.

In order to use a compound of Structure (1) for the therapeutic treatment of humans and animals, it is normally formulated in accordance with standard pharmaceutical practice as a pharmaceutical composition. Therefore in another aspect the present invention provides a pharmaceutical composition which comprises a compound of Structure (1) and a pharmaceutically acceptable carrier.

The compounds of the Structure (1) may be administered in standard manner for the treatment of the indicated diseases, for example orally, parenterally, rectally, trans-dermally or via trans-mucosal (for example sub-lingual, or buccal or insufflatory) administration.

The compounds of the Structure (1) which are active when given orally or via sub-lingual or buccal administration can be formulated as syrups, tablets, capsules and lozenges. A syrup formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be utilised, for example aqueous gums, celluloses, silicates or oils and are incorporated in a soft gelatin capsule shell.

Typical parenteral compositions consist of a solution or suspension of the compound of the Structure (1) in a sterile aqueous or non-aqueous carrier optionally containing a parenterally acceptable oil, for example polyethylene glycol, polyvinylpyrrolidone, lecithin, arachis oil, or sesame oil.

A typical suppository formulation comprises a compound of Structure (1) which is active when administered in this way, with a binding and/or lubricating agent, for example polymeric glycols, gelatins, cocoabutter or other low melting vegetable waxes or fats.

Typical transdermal formulations comprise a conventional aqueous or non-aqueous vehicle, for example a cream, ointment, lotion or paste or can be in the form of a medicated plaster, patch or membrane.

Preferably the composition is in unit dosage form, for example a tablet or capsule, so that the patient may administer to himself a single dose.

Piracetam is a compound which is used in the treatment of senile dementia and related disease conditions. The compounds of Structure (1) can be administered in similar regimes to those established for piracetam with any appropriate adjustment in dose levels or frequency of dosing having regard to the greater activity and better pharmacological profile of the compounds of Structure (1).

Each dosage unit for oral administration contains suitably from 0.5 mg/Kg to 50 mg/Kg, and preferably from 1 mg/Kg to 8 mg/Kg, and each dosage unit for parenteral administration contains suitably from 0.1 mg/Kg to 10 mg/Kg, of a compound of Structure (1).

The daily dosage regimen for oral administration is suitably about 0.5 mg/Kg to 100 mg/Kg, more suitably about 1 mg/Kg to 25 mg/Kg of a compound of Structure (1) calculated as the free base. The active ingredient may be administered from 1 to 6 times daily. The compounds of Structure (1) may be co-administered with other pharmaceutically active compounds, for example in combination, concurrently or sequentially, particularly with other compounds used in the treatment of elderly patients e.g. tranquillisers, diuretics antihypertensives, vasodilator and inotropic agents.

The invention is illustrated by the following Examples.

EXAMPLE 1

A. (1) To an ice-cold stirred solution of 2,2-dimethyl-4-imidazolidinone (7 g) and potassium carbonate (12.8 g) in water (80 ml), bromoacetyl bromide (5.4 ml) was added dropwise. The reaction mixture was stirred at the same temperature for 1 hour, then at room temperature for 2 hours. The obtained suspension was extracted three times with ethyl acetate and the organic phase was washed with 3% hydrochloric acid, dried and evaporated under reduced pressure to give a residue which was crystallized from xylene to afford 1-(2-bromoacetyl)-2,2-dimethyl-4-imidazolidinone as a white crystalline powder, m.p. 137°–138° C.

Using chloroacetyl chloride in a similar procedure gave 1-(2-chloroacetyl)-2,2-dimethyl-4-imidazolidinone as a white powder, m.p. 151°–153° C. (diethyl ether).

(2) A solution of 1-(2-bromoacetyl)-2,2-dimethyl-4-imidazolidinone (2 g) in 33% ammonia solution (80 ml) was stirred at room temperature overnight. After evaporation under reduced pressure, the residue was dissolved in dry ethanol and evaporated again to give 1-(2-aminoacetyl)-2,2-dimethyl-4-imidazolidinone hydrobromide as a white deliquescent powder (Rf 0.33, n-butanol/water/acetic acid 6:2:2, silica gel plates). The latter compound can also be prepared using the chloroacetyl derivative in a similar procedure.

B. (1)
1-[2-(Benzyloxycarbonylamino)acetyl]-2,2-dimethyl-4-imidazolidinone

To an ice-cold solution of N-(benzyloxycarbonyl) glycine (9 g) and 2,2-dimethyl-4-imidazolidinone (5 g) in tetrahydrofuran (THF) (150 ml) a solution of dicyclohexylcarbodiimide (DCC) (9 g) in THF (50 ml) was added dropwise. After stirring for 3 hours at 20° C., the precipitate was filtered off, the filtrate was evaporated to dryness and the residue was crystallized from 2-propanol affording 12 g of the title compound, m.p. 135°–136° C.

(2) 1-(2-Aminoacetyl)-2,2-dimethyl-4-imidazolidinone

Into a solution of the preceding compound (12 g) in methanol (300 ml), containing 5% palladium on charcoal (2.4 g), hydrogen was bubbled at 20° C. and atmospheric pressure for 1.5 hours. Removal of the catalyst and evaporation of the solvent gave a residue which was triturated with ethyl acetate to afford 5.3 g of the title compound, m.p. 145°–148° C.

EXAMPLE 2

(1)
1-[2-(Benzyloxycarbonylamino)acetyl]-2-isopropyl-4-imidazolidinone

Into an ice-cold solution of N-(benzyloxycarbonyl) glycine (26 g) and 2-isopropyl-4-imidazolidinone (16 g) in THF (260 ml), a solution of DCC (25.4 g) in THF (100 ml) was added dropwise. After stirring for 2 hours at 20° C., the precipitate was filtered off and the filtrate was evaporated to dryness. Crystallization of the residue from 2-propanol yielded 33.5 g of the title compound, m.p. 137°–139° C.

(2) 1-(2-Aminoacetyl)-2-isopropyl-4-imidazolidinone

Into a solution of the preceding compound (33 g) in methanol (500 ml) containing 5% palladium on charcoal (6 g), hydrogen was bubbled at 20° C. and at atmospheric pressure for 2 hours. Removal of the catalyst and evaporation of the solvent gave a residue which was crystallized from 2-propanol affording 15 g of the title compound, m.p. 141°–143° C.

EXAMPLE 3

(1)
1-[2-(Benzyloxycarbonylamino)propanoyl]-2,2-dimethyl-4-imidazolidinone

To a stirred, ice-cold solution of N-(benzyloxycarbonyl)alanine (6.7 g) and 2,2-dimethyl-4-imidazolidinone (3.42 g) in 100 ml of THF, a solution of DCC (6.2 g) in 50 ml of THF was added dropwise during 15 minutes. The suspension was stirred at 0° C. for 2 hours and at room temperature for an additional 2 hours. The insoluble material was filtered off. The solvent was evaporated under reduced pressure. Crystallization of the residue from isopropanol gave the title product as a white powder m.p. 170°–171° C.

(2)
1-(2-Aminopropanoyl)-2,2-dimethyl-4-imidazolidinone

An ethanolic solution of 1-[2-(benzyloxycarbonylamino)propanoyl]-2,2-dimethyl-4-imidazolidinone (4.9 g) containing 1 g of 5% palladium on charcoal was stirred at room temperature while hydrogen was bubbled into the solution for 1 hour. Removal of the catalyst, evaporation of the solvent, and trituration of the residue with ethyl acetate afforded the title compound as a white powder m.p. 156° C. (decomp).

EXAMPLE 4

1-(2-Benzylaminoacetyl)-2,2-dimethyl-4-imidazolidinone

A solution of 1-(2-bromoacetyl)-2,2-dimethyl-4-imidazolidinone (1.9 g) in 8.8 ml of benzylamine was stirred at room temperature for 4 hours. The excess of benzylamine was removed under reduced pressure (about 5 mmHg) at 80° C. The residue was taken up with ethyl acetate and the precipitate filtered off. The filtrate was evaporated and the residue was chromatographed on a silica gel column by eluting with dichloromethane/methanol 7:3. The selected fractions were collected and evaporated. Trituration of the residue with ether gave 1 g of the title compound as a white powder, m.p. 131°–132° C.

EXAMPLE 5

(A) (1) To an ice-cold solution of thionyl chloride (5 ml) in dry ethanol (50 ml) a solution of sodium 2,2-dimethyl-5-oxo-1-imidazolidineacetate (4 g) in dry ethanol (50 ml) was added dropwise. The mixture was stirred at 0° C. for 1 hour, then at room temperature overnight. After evaporation under reduced pressure, the residue was taken up with a saturated solution of sodium hydrogen carbonate and extracted with 3×100 ml of dichloromethane. The organic layer was dried and evaporated, to yield ethyl 2,2-dimethyl-5-oxo-1-imidazolidineacetate (2.57 g) as a colorless oil (Rf. 0.49, methanol/acetone 1:1; silica gel plates). Oxalate salt m.p. 109°–113° C. (ethanol/diethyl ether).

(2) An ice-cold solution of ethyl 2,2-dimethyl-5-oxo-1-imidazolidineacetate (2 g) in methanol (150 ml) was saturated with gaseous ammonia). The solution was stirred at room temperature for 36 hours. After evaporation the residue was chromatographed on a silica gel column, eluting with dichloromethane/methanol 6:4. The selected fractions were collected, evaporated and the residue was crystallized from ethanol, to give 2,2-dimethyl-5-oxo-1-imidazolidineacetamide (1 g) as a white powder, m.p. 144°–146°.

(B) (1) To a solution of glycylglycinamide acetate (10 g) in methanol (250 ml) and acetone (125 ml), Amberlite IRA-68 resin (20 g) (from Rohm & Haas, Philadelphia, USA) was added. Amberlite is a registered trade mark and IRA-68 is a weakly basic resin. The suspension was stirred at room temperature for 1 hour, then resin was filtered off and the solution was evaporated under reduced pressure. The residue was suspended in refluxing acetone (250 ml) and methanol was added to obtain a clear solution, which was refluxed for 2 hours. Evaporation and trituration of the residue with acetone gave 2,2-dimethyl-5-oxo-1-imidazolidineacetamide (6.85 g).

(2) An ice cold solution of 2,2-dimethyl-5-oxo-1-imidazolidineacetamide (1 g) in 20 ml of saturated solution of sodium hydrogen carbonate was added with an additional 2 g of sodium hydrogen carbonate and treated dropwise with chloroacetyl chloride (3 ml). After 30 minutes of stirring the precipitate was collected and crystallized from methanol, to give 3-(2-chloroacetyl)-2,2-dimethyl-5-oxo-1-imidazolidineacetamide (0.53 g) as a white powder m.p. 214°–216° C.

(3) A suspension of 3-(2-chloroacetyl)-2,2-dimethyl-5-oxo-1-imidazolidineacetamide (0.48 g) in 33% ammonia solution (6 ml) was stirred at room temperature for 90 minutes. The clear solution obtained was diluted with dry ethanol (80 ml) and evaporated under reduced pressure. The residue was crystallized from water/acetone to afford 3-(2-aminoacetyl)-2,2-dimethyl-5-oxo-1-imidazolidine acetamide hydrochloride as a white powder, m.p. 292° C. decomp.

EXAMPLE 6

2,2-Dimethyl-1-(2-oxo-1-pyrrolidineacetyl)-4-imidazolidin-one

An ice cold solution of 2-oxo-1-pyrrolidineacetic acid (2.2 g) and triethylamine (2.15 ml) in dimethylformamide (10 ml) was treated dropwise while stirring with butyl chloroformate (1.95 ml). After stirring at 0° C. for 30 minutes, 2,2-dimethyl-4-imidazolidinone (1.75 g) was added at once, and stirring was continued at room temperature overnight. After evaporation under reduced pressure the residue was chromatographed on a silica gel column, eluting with dichloromethane/methanol 1:1. The selected fractions were collected and evaporated to give an oil which was washed twice with ethyl acetate. The residue was crystallized from ethyl acetate, to give the title compound as a white powder, m.p. 214°–217° C. (decomp.).

EXAMPLE 7

2,2-Dimethyl-5-oxo-3-(2-oxo-1-pyrrolidineacetyl)-1-imidazolidineacetamide

An ice cold solution of 2-oxo-1-pyrrolidineacetic acid (1.45 g) and triethylamine (1.45 ml) in dimethylformamide (7 ml) was treated dropwise while stirring with butyl chloroformate (1.3 ml). After stirring at 0° C. for 45 minutes, 2,2-dimethyl-5-oxo-1-imidazolidineacetamide (1.75 g) was added at once and stirring was prolonged at room temperature overnight. After evaporation under reduced pressure, the residue was chromatographed on a silica gel column, eluting with dichloromethane/methanol 1:1. The selected fractions were collected and evaporated, the residue was taken up with ethyl acetate and the resulting solid was crystallized from ethanol, to give the title compound as a white powder, m.p. 225°–227° C., (decomp.).

EXAMPLE 8

2,2-Dimethyl-1-[2-(2-oxo-1-pyrrolidineacetamido)acetyl]-4-imidazolidinone

An ice cold solution of 2-oxo-1-pyrrolidineacetic acid (1.03 g) and triethylamine (1.01 ml) in dichloromethane (20 ml) was treated dropwise with butyl chloroformate (0.92 ml). After stirring at 0° C. for 30 minutes a suspension of 1-(2-aminoacetyl)-2,2-dimethyl-4-imidazolidinone hydrobromide (1.82 g) and triethylamine (1.01 ml) in dichloromethane (20 ml) was added, and the temperature was gradually raised to room temperature. After stirring at room temperature for 1 day the suspension was evaporated under reduced pressure. The residue was chromatographed on a silica/gel column eluting with methanol/dichloromethane 1:1. The selected fractions were collected and evaporated, the residue was washed with ethyl acetate and crystallized from ethanol to give the title compound as a white solid, m.p. 229°–231° C.

EXAMPLE 9

(1) Isobutyl 4-[(N-benzyl)-[N-(2,2-dimethyl-4-oxo-1-imidazolidine)-carbonylmethyl]amino]-3-hydroxybutanoate 1-(2-Benzylaminoacetyl)-2,2-dimethyl-4-imidazolidinone (950 mg) was dissolved in an excess of isobutyl 3,4-epoxybutanoate (2.3 ml) by heating under stirring at 80° C. for 3 hours. The mixture was then chromatographed on a silica gel column by eluting with dichloromethane/methanol 9:1 to obtain 3 g of a crude oil. The oil was washed three times with light petroleum and dried under vacuum to give 1.5 g of the title compound as a colorless oil (Rf.0.48, dichloromethane/methanol 9:1; silica gel plates). Mass spectrum (E.I., 70 eV, 1.5 mA), m/z=404 (M.+—CH$_3$), 279.

(2) Isobutyl 4-[N-[(2,2-dimethyl-4-oxo-1-imidazolidine)carbonylmethyl]amino]-3-hydroxybutanoate An ethanol solution of isobutyl 4-[(N-benzyl)-[N-(2,2-dimethyl-4-oxo-1-imidazolidine)carbonylmethyl]amino]-3-hydroxybutanoate (1.3 g) containing 200 mg of 5% palladium on charcoal was stirred at room temperature under 30 p.s.i. (207×10$^3$ Pa) of hydrogen for 1 hour. Removal of the catalyst and evaporation of the solvent afforded 1 g of the title compound as an oil (Rf. 0.44, dichloromethane/methanol 8:2; silica gel plates). Mass spectrum (E.I., 70 eV, 1.5 mA), m/z=188 (M.+—C$_6$H$_9$N$_2$O$_4$), 114.

(3) 2,2-dimethyl-1-(4-hydroxy-2-oxo-1-pyrrolidineacetyl)-4-imidazolidinone

A solution of isobutyl 4-[N-[(2,2-dimethyl-4-oxo-1-imidazolidine)carbonylmethyl]amino]-3-hydroxybutanoate (1 g) in n-amyl alcohol (10 ml) was refluxed under nitrogen for 8 hours. The solution was cooled to room temperature and the precipitate was collected and crystallized from isopropanol to give the title compound, as a white powder, m.p. 253° C. (decomp).

EXAMPLE 10

2,2-Dimethyl-5-oxo-3-(4-hydroxy-2-oxo-1-pyrrolidineacetyl)-1-imidazolidineacetamide To a stirred solution of 4-hydroxy-2-oxo-1-pyrrolidine acetic acid (3.18 g) and 2,2-dimethyl-5-oxo-1-imidazolidineacetamide (3.5 g) in 100 ml of dimethylformamide at room temperature, 4.12 g of DCC were added at once. After 5 hours the solvent was evaporated under vacuum and the residue was suspended in 50 ml of stirred water. After 10 minutes the solid was filtered off and the water evaporated under reduced pressure. The residue was triturated with isopropanol and collected, affording the title product as a white powder m.p. 248°-250° C. (decomp).

EXAMPLE 11

2,2-Dimethyl-1-[2-(4-hydroxy-2-oxo-1-pyrrolidineacetamido)acetyl]-4-imidazolidinone Into an ice cold solution of 4-hydroxy-2-oxo-1-pyrrolidineacetic acid (0.95 g) and 1-(2-aminoacetyl)-2,2-dimethyl-4-imidazolidinone (1 g) in dimethylsulfoxide (30 ml) a solution of DCC (1,22 g) in tetrahydrofuran (10 ml) was added dropwise. The solution was stirred at room temperature overnight and then heated at 50° for 4 hours. After cooling the solution was diluted with water and the resulting precipitate was filtered off. The filtrate was evaporated to dryness under vacuum. The residue was dissolved in water and eluted on a column of Amberlite IR 120H (20 ml). The eluate was treated with Amberlite IRA 68 (10 ml), filtered and evaporated under vacuum. The residue was triturated with isopropanol to yield 0.4 g of the title compound, m.p. 227°-229°.

EXAMPLE 12

2-(1-Methylethyl)-1-(2-oxo-1-pyrrolidineacetyl)-4-imidazolidinone

The same procedure of Example 10 starting from 2-oxo-1-pyrrolidineacetic acid and 2-(1-methylethyl)-4-imidazolidinone afforded the title compound as a white powder, m.p. 188°-191° C. (2-propanol).

EXAMPLE 13

4-(4-Hydroxy-2-oxo-1-pyrrolidineacetyl)-1,4-diazaspiro-[4,5]-decan-2-one

The same procedure of Example 10 starting from 4-hydroxy-2-oxo-1-pyrrolidineacetic acid and 1,4-diazaspiro[4,5]-decan-2-one afforded the title compound as a white powder, m.p. 285°-286° C. (water).

EXAMPLE 14

1-[2-[2-(2-Aminoacetamido)acetamido]acetyl]-2,2-dimethyl]-4-imidazolidinone

Into an ice-cold suspension of N-(benzyloxycarbonyl)glycylglycine (6.6 g) and 1-(2-aminoacetyl)-2,2-dimethyl-4-imidazolidinone (4 g) in tetrahydrofuran (150 ml) and dimethylsulfoxide (50 ml ), a solution of DCC (5.3 g) in acetonitrile (50 ml) was added dropwise. After stirring for 2 days at 20° C., the volatile solvents were evaporated under vacuum. The residue was diluted with water, the precipitate was filtered off, and the filtrate was concentrated to small volume under vacuum. The residue was diluted with brine and extracted with n-pentanol. The organic solution was evaporated to dryness and the residue was dissolved in methanol (300 ml).

5% Palladium on charcoal (2 g) was added to the solution and hydrogen was bubbled for 2 hours at 20° C. and at atmospheric pressure. Removal of the catalyst and evaporation of the solvent gave a residue which, after crystallization from 2-propanol, yielded 2.5 g of the title compound, m.p. 164°-166° C.

EXAMPLE 15

2,2-Dimethyl-1-[2-(2-isopropyl-5-oxo-1-imidazolidineacetamido)acetyl]-4-imidazolidinone A solution of 1-[2-[2-(2-aminoacetamido)acetamido]acetyl]-2,2-dimethyl-4-imidazolidinone (0.5 g) and isobutyraldehyde (0.18 ml) in methanol (5 ml) was refluxed for 0.5 hours.

Evaporation of the solvent gave the title compound as a waxy solid, Rf 0.33 (dichloromethane/methanol 8:2, silica gel plates). Oxalate salt (from 2-propanol): m.p. 95° C. (sinters) 112° C. decomp.

EXAMPLE 16

2,2-Dimethyl-1-[2-(2,2-dimethyl-5-oxo-1-imidazolidineacetamido)acetyl]-4-imidazolidinone A solution of 1-[2-[2-(2-aminoacetamido)acetamido]-2,2-dimethyl-4-imidazolidinone (0.5 g) in methanol (3 ml) and acetone (7 ml) was refluxed for 3 hours. Evaporation of the solvent and trituration with diisopropyl ether yielded 0.3 g of the title compound as a waxy solid, Rf=0.23 (dichloromethane/methanol 8:2, silica gel plates). Perchlorate salt, m.p. 95° C. dec.

EXAMPLE 17

1-(2-Aminoacetyl)-2,2,5-trimethyl-4-imidazolidinone

The same procedure of the Example 2, starting from N-benzyloxycarbonylglycine and 2,2,5-trimethyl-4-imidazolidinone (m.p. 74°–75° C.; obtained from DL-alaninamide and acetone), afforded 1-(2-benzyloxycarbonylaminoacetyl)-2,2,5-trimethyl-4-imidazolidinone, m.p 170°–171° C., then the title compound m.p. 161°–163° C. dec. Mass spectrum (C.I., i—$C_4H_{10}$, 70 eV, 1.5 mA), m/z=186 (MH+).

EXAMPLE 18

(1) 2-Isopropyl-5-methyl-4-imidazolidinone

2-Isopropyl-5-methyl-4-imidazolidinone was obtained from DL-alaninamide and isobutyraldehyde, m.p. 67°–69° C. Rf=0.35 (dichloromethane-methanol 9:1, silica gel plates). Mass spectrum (E.I., 70 eV, 1.5 mA), m/z=99 (M.+—$C_3H_7$).

(2) 1-(2-Aminoacetyl)-2-isopropyl-5-methyl-4-imidazolidinone

The same procedure of the example 2, starting from N-benzyloxycarbonylglycine and 2-isopropyl-5-methyl-4-imidazolidinone afforded 1-(2-benzyloxycarbonylaminoacetyl)-2-isopropyl-5-methyl-4-imidazolidinone as a diastereoisomeric mixture Rf=0.52 and 0.57 (dichloromethane/methanol 9:1, silica gel plates) then the oily title compound as a diastereoisomeric mixture, Rf=0.24 and 0.27 (dichloromethane/methanol 7:3, silica gel plates). Mass spectrum (E.I., 70 e V, 1.5 mA), m/z=156 (M.+—$C_3H_7$).

EXAMPLE 19

1-[2-(2S-Amino-4-methylpentanamido)acetyl]-2,2-dimethyl-4-imidazolidinone

The same procedure of the Example 2, starting from (L)-N-benzyloxycarbonylleucine and 2,2-dimethyl-1-(2-aminoacetyl)-4-imidazolidinone afforded 1-[2-(2S-benzyl-oxycarbonylamino-4-methylpentanamido)acetyl]-2,2-dimethyl-4-imidazolidinone, m.p. 76°–80° C., [alpha]$_D$=−22.4° (c=1, MeOH), then the title compound, m.p. 143°–145° C.; [alpha]$_D$=+33.0° (c=1; 0.1N HCl). Mass spectrum (E.I., 70 eV, 1.5 mA), m/z=284 (M.+), 269 (M.+-15).

EXAMPLE 20

1-(2-Acetamidoacetyl)-2,2-dimethyl-4-imidazolidinone

A suspension of 1-(2-aminoacetyl)-2.2-dimethyl-4-imidazolidinone (5 g) in acetic anhydride (20 ml) was stirred at room temperature for 1 hour. Evaporation under vacuum and crystallization of the residue from 2-propanol gave 4.63 g of the title compound, m.p. 214°–215° C.

EXAMPLE 21

3-(2-Aminopropionyl)-2,2-dimethyl-5-oxo-1-imidazolidineacetamide

To a stirred, ice cold solution of N-(benzyloxycarbonyl)alanine (6.7 g) and 2,2-dimethyl-5-oxo-1-imidazolidineacetamide (5.2 g) in 100 ml of dimethylformamide (DMF), a solution of dicyclohexylcarbodiimide (DCC) (6.2 g) in 50 ml of DMF was added dropwise during 15'. The suspension was stirred at 0° C. for 2 hours and at room temperature for additional 2 hours. The insoluble material was filtered off, the solvent was evaporated under reduced pressure, affording crude 3-[2-(benzyloxycarbonylamino)propionyl]-2,2-dimethyl-5-oxo-1-imidazolidineacetamide m.p. 206°–210° C. Into a solution of this compound (3 g) in methanol (100 ml) containing 5% palladium on charcoal (0.6 g) hydrogen was bubbled at 20° C. for 1.5 hours. Removal of catalyst and evaporation of the solvent gave a residue which was triturated with ethanol to afford the title compound, m.p. 196°–197° C.

EXAMPLE 22

3-(2-Aminoacetyl)-2-isopropyl-5-oxo-1-imidazolidineacetamide (1) To an ice cold solution of thionyl chloride (2 ml) in dry ethanol (50 ml) sodium 2-isopropyl-5-oxo-1-imidazolidineacetate(2.1g) was added. The suspension was stirred at 0° C. for 1 hour and stirring was continued at room temperature for 2 hours. The solvent was evaporated under reduced pressure and the residue was treated with ethyl acetate. The insoluble material was filtered off and the solvent evaporated. The residue was dissolved in a saturated solution of sodium hydrogen carbonate and extracted three time with dichloromethane (50 ml). The organic layer was dried and evaporated to afford ethyl 2-isopropyl-5-oxo-1-imidazolidineacetate (0.9 g) as pale yellow oil (Rf 0.6, ethyl acetate/-dichloromethane 6:4, silica gel plates). Hydrochloride salt, m.p. 148°–149° C. (methanol/ethylacetate).

(2) An ice cold solution of ethyl 2-isopropyl-5-oxo-1-imidazolidineacetate (3.8 g) in methanol (100 ml) was saturated with gaseous ammonia. The solution was stirred at room temperature overnight and the solvent was removed under reduced pressure yielding 2-isopropyl-5-oxo-1-imidazolidineacetamide as viscous oil (Rf 0.33; ethyl acetate/methanol 6:4, silica gel plates). Sulphate monohydrate salt, m.p. 64° C., resolidifing and final decomposition at 114°–118° C.

(3) The same procedure of Example 5 (method B), starting from 2-isopropyl-5-oxo-1-imidazolidineacetamide, afforded 3-(2-chloroacetyl)-2-isopropyl-5-oxo-1-imidazolidineacetamide, m.p. 163° C., then the title compound as hygroscopic hydrochloride, m.p. 205°–211° C. Mass spectrum (E.I., 70 eV, 1.5 mA), m/z=199 (M.+—$C_3H_7$).

EXAMPLE 23

3-(2-Aminoacetyl)-2,2,4-trimethyl-5-oxo-1-imidazolidineacetamide (1) A solution of (DL)-alanylglycineamide (8 g) in acetone (100 ml) was stirred at room temperature for 24 hours, then was refluxed for 1 hour. The solid residue was filtered off and the solvent was evaporated. The residue (10 g) was treated at 0° C. with a saturated solution of maleic acid (30 ml) to give 2,2,4-trimethyl-5-oxo-1-imidazolidine-acetamide maleate, as white solid, m.p. 145°–148° C. (dec).

(2) The same procedure of Example 2, starting from 2,2,4- trimethyl-5-oxo-1-imidazolidineacetamide and N-benzyloxycarbonylglycine, afforded 3-(2-benzyloxycarbonylaminoacetyl)-2,2,4-trimethyl-5-oxo-1-imidazolidineacetamide, as an oil, then the title compound, m.p. 118° C. Mass spectrum (E.I., 70 eV, 1.5 mA), m/z=212 (M.+—$CH_4N$), 184 (M.+—$C_2H_4NO$).

Example 24

3-(2-Acetamidoacetyl)-2,2-dimethyl-5-oxo-1-imidazolidineacetamide

A solution of 3-(2-aminoacetyl)-2,2-dimethyl-5-oxo-1-imidazolidineacetamide (2 g) in acetic anhydride (10 ml) was stirred at 80° C. for 5 minutes. After cooling, the precipitate was collected and washed with acetone, affording the title compound as a white powder, m.p. 222° C. dec.

EXAMPLE 25

2-Isopropyl-1-[2-(2-oxo-1-pyrrolidineacetamido)acetyl]4-imidazolidinone

A mixture of ethyl 2-oxo-1-pyrrolidineacetate (7 g) and 1-(2-aminoacetyl)-2-isopropyl-4-imidazolidinone (4 g) was heated at 110° C. for 8 hours. After cooling the oily residue was chromatographed on a silica gel column (eluant dichloromethane/methanol 9:1). The selected fractions were collected, evaporated under vacuum and the residue was triturated with diisopropyl ether to yield 2.6 g of the title compound, m.p. 104°-106° C. Mass spectrum (E.I., 70 eV, 1.5 mA), m/z=310 (M.+), 267 (M.+—$C_3H_7$).

EXAMPLE 26

2,2-Dimethyl-1-[2-(2-oxo-1-pyrrolidineacetamido)propionyl]4-imidazolidinone

The same procedure of Example 25, starting from ethyl 2-oxo-1-pyrrolidineacetate and 1-(D,L-alanyl)-2,2-dimethyl-4-imidazolidinone, afforded the title compound, m.p. 198°-200° C. (2-propanol).

EXAMPLE 27

2,2-Dimethyl-1-(4-hydroxy-2-oxo-1-pyrrolidineacetyl)-4-imidazolidinone

The same procedure of Example 10, starting from 4-hydroxy-2-oxo-1-pyrrolidineacetic acid and 2,2-dimethyl-4-imidazolidinone, afforded the title compound, m.p. 250° C. (dec).

EXAMPLE 28

1-[2-(2-Oxo-1-pyrrolidineacetamido)acetyl]-2,2,5-trimethyl-4-imidazolidinone

The same procedure of example 11, starting form 2-oxo-1-pyrrolidineacetic acid and 1-(2-aminoacetyl)-2,2,5-trimethyl-4-imidazolidinone, gave the title compound, m.p. 213°-215° C. dec.

EXAMPLE 29

2-Isopropyl-5-methyl-1-]2-(2-oxo-1-pyrrolidineacetamido)acetyl]-4-imidazolidinone The same procedure of example 11 starting from 2-oxo-1-pyrrolidineacetic acid and 1-(2-aminoacetyl)-2-isopropyl-5-methyl-4-imidazolidinone gave the title compound as a diastereoisomeric mixture, m.p. 188°-194° C. Mass spectrum (E.I., 70 eV, 1.5 mA), m/z=324 (M.+), 281 (M.+—$C_3H_7$).

EXAMPLE 30

2,2-Dimethyl-1-[2-(2,2-dimethyl-4-isobutyl-5-oxo-1-imidazolidine)acetyl]-4-imidazolidinone The same procedure of example 16, starting from 1-[2-(2S-amino-4-methylpentanamido)acetyl]-2,2-dimethyl-4-imidazolidinone afforded the title compound as a foamy solid, which has no definite melting point and decomposes at 124° C. Rf=0.23 (dichloromethane-methanol 9:1, silica gel plates). [alpha]$_D$ = —14.1° (c=1, MeOH); [alpha]$_D$=—19.0° (c=1, 0.1N HCl). Mass spectrum (E.I., 70 eV, 1.5 mA), m/z=324 (M.+), 309 (M.+-15).

EXAMPLE 31

1-[2-(4-Hydroxy-2-oxo-1-pyrrolidineacetamido)acetyl]-2,2,5-trimethyl-4-imidazolidinone The same procedure of Example 11, starting from 4-hydroxy-2-oxo-1-pyrrolidineacetic acid and 1-(2-aminoacetyl)-2,2,5-trimethyl-4-imidazolidinone, gave the title compound as a diastereoisomeric mixture, m.p. 218°-220° C. Mass spectrum (E.I., 70 eV, 1.5 mA), m/z=269 (M.+—$C_3H_7N$).

EXAMPLE 32

Composition for 1 tablet

| | |
|---|---|
| 3-(2-aminoacetyl)-2,2-dimethyl-5-oxo-1-imidazolidineacetamide | 100 mg |
| lactose | 100 mg |
| corn starch | 80 mg |
| talcum | 11.5 mg |
| silicon dioxide | 4 mg |
| magnesium stearate | 2.5 mg |
| gelatine | 2.0 mg |

For the manufacture of 1000 tablets, 100 g of active ingredient are mixed with 100 g of lactose and 70 g of corn starch. The mixture is moistened with an aqueous solution of gelatine and then granulated and dried. The granules are mixed with 10 g of corn starch, 11.5 g of talcum, 4.0 g of silicon dioxide and 2.5 g of magnesium stearate and the mixture is pressed into tablets each weighing 300 mg and having the active ingredient content of 100 mg. The tablets can have different shapes and breaking notches for finer adjustment of the dosage.

What is claimed is:

1. A compound of Structure (1):

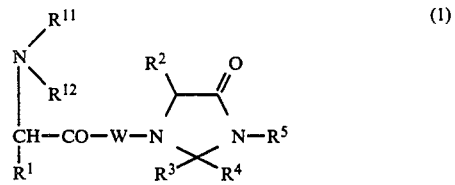

in which $R^1$ is H, $C_{1-5}$alkyl (straight or branched), or phenyl;

W is a bond, —NHCHR$^6$CO— or —NHCHR$^6$CONHCHR$^7$CO—, where R$^6$ and R$^7$, which can be the same or different are H or $C_{1-5}$alkyl (straight or branched);

R$^2$ is H, $C_{1-5}$alkyl (straight or branched), $C_6$-$C_{10}$ aryl or a benzyl group optionally substituted by $C_{1-5}$ alkyl (straight or branched), $C_{1-4}$ alkoxy (straight or branched) or hydroxy;

R$^3$ and R$^4$, which can be the same or different, are H, $C_{1-5}$alkyl (straight or branched) or phenyl, or R$^3$ and R$^4$ are taken together to form a 1,4-butylene or 1,5-pentylene group;

R$^5$ is H or —CHR$^8$CONR$^9$R$^{10}$, where R$^8$, R$^9$ and R$^{10}$, which can be the same or different, are H or $C_{1-5}$alkyl (straight or branched);

$R^{11}$ and $R^{12}$, which can be the same or different, are H, $C_{1-5}$alkyl (straight or branched), benzyl or lower alkanoyl or $C_7$-$C_{11}$ aroyl taken together with the nitrogen atom shown to form a 2-oxopyrrolidino group optionally substituted in the 4-position by a hydroxy or $C_{1-5}$ (straight or branched) alkoxy group, or a 5-oxo-1-imidazolidine group optionally substituted at the 2- position by one or two $C_{1-5}$ alkyl groups or a 1,4-butylene or 1,5-pentylene group, or optionally substituted at the 4-position by $C_{1-5}$ alkyl, or a pharmaceutically acceptable salt thereof.

2. A compound according to claim 1 in which $R^1$ is selected from the group consisting of H, methyl and isobutyl.

3. A compound according to claim 1 in which $R^2$ is hydrogen or methyl.

4. A compound according to claim 3 in which $R^3$ and $R^4$ are both methyl or taken together to form a 1,4-butylene or 1,5-pentylene group, or $R^3$ is isopropyl and $R^4$ is hydrogen.

5. A compound according to claim 4 in which $R^5$ is H or $CH_2CONH_2$.

6. A compound according to claim 5 in which $R^8$ is selected from the group consisting of H, methyl, isopropyl, 1-methylpropyl and isobutyl.

7. A compound according to any one of claim 6 in which $R^9$ is selected from the group consisting of H, methyl, isopropyl, 1-methylpropyl and isobutyl.

8. A compound according to claim 7 in which $R^{10}$ is selected from the group consisting of H, methyl, isopropyl, 1-methylpropyl and isobutyl.

9. A compound according to any one of claim 1 which is:
3-(2-aminoacetyl)-2,2-dimethyl-5-oxo-1-imidazolidine acetamide, or
2,2-dimethyl-1-[2-(2-oxo-1-pyrrolidineacetamido)acetyl]-4-imidazolidinone.

10. A compound according to claim 1 selected from the group consisting of:
1-(2-aminoacetyl)-2,2-dimethyl-4-imidazolidinone,
1-(2-aminoacetyl)-2-isopropyl-4-imidazolidinone,
1-(2-aminopropanoyl)-2,2-dimethyl-4-imidazolidinone,
1-(2-benzylaminoacetyl)-2,2-dimethyl-4-imidazolidinone,
2,2-dimethyl-1-(2-oxo-1-pyrrolidineacetyl)-4-imidazolidinone,
2,2-dimethyl-5-oxo-3-(2-oxo-1-pyrrolidineacetyl)-1-imidazolidineacetamide,
2,2-dimethyl-1-(4-hydroxy-2-oxo-1-pyrrolidineacetyl)-4-imidazolidinone,
2,2-dimethyl-5-oxo-3-(4-hydroxy-2-oxo-1-pyrrolidineacetyl)-1-imidazolidineacetamide,
2,2-dimethyl-1-[2-(4-hydroxy-2-oxo-1-pyrrolidineacetamido)acetyl]-4-imidazolidinone,
2-isopropyl-1-(2-oxo-1-pyrrolidineacetyl-4-imidazolidinone,
4-(4-hydroxy-2-oxo-1-pyrrolidineacetyl)-1,4-diazaspiro[4,5]-decan-2-one,
1-[2-[2-(2-aminoacetamido)acetamido]acetyl]-2,2-dimethyl]-4-imidazolidinone,
2,2-dimethyl-1-[2-(2-isopropyl-5-oxo-1-imidazolidineacetamido)acetyl]-4-imidazolidinone,
2,2-dimethyl-1-[2-(2,2-dimethyl-5-oxo-1-imidazolidineacetamido)acetyl]-4-imidazolidinone,
1-(2-aminoacetyl)-2,2,5-trimethyl-4-imidazolidinone,
1-(2-aminoacetyl)-2-isopropyl-5-methyl-4-imidazolidinone,
1-[2-(2S-amino-4-methylpentanamido)acetyl]-2,2-dimethyl-4-imidazolidinone,
1-(2-acetamidoacetyl)-2,2-dimethyl-4-imidazolidinone,
3-(2-aminopropionyl)-2,2-dimethyl-5-oxo-1-imidazolidineacetamide,
3-(2-aminoacetyl)-2-isopropyl-5-oxo-1-imidazolidineacetamide,
3-(2-aminoacetyl)-2,2,4-trimethyl-5-oxo-1-imidazolidineacetamide,
3-(2-acetamidoacetyl)-2,2-dimethyl-5-oxo-1-imidazolidineacetamide,
2-isopropyl-1-[2-(2-oxo-1-pyrrolidineacetamido)acetyl]-4-imidazolidinone,
2,2-dimethyl-1-[2-(2-oxo-1-pyrrolidineacetamido)propionyl]-4-imidazolidinone,
2,2-dimethyl-1-(4-hydroxy-2-oxo-1-pyrrolidineacetyl)-4-imidazolidinone,
1-[2-(2-oxo-1-pyrrolidineacetamido)acetyl]-2,2,5-trimethyl-4-imidazolidinone,
2-isopropyl-5-methyl-1-[2-(2-oxo-1-pyrrolidineacetamido)acetyl]-4-imidazolidinone,
2,2-dimethyl-1-[2-(2,2-dimethyl-4-isobutyl-5-oxo-1imidazolidine)acetyl]-4-imidazolidinone, and
1-[2-(4-hydroxy-2-oxo-1-pyrrolidineacetamido)acetyl]-2,2,5-trimethyl-4-imidazolidinone.

11. A nootropic pharmaceutical composition comprising an effective amount of a compound according to any one of claims 1 to 10 and a pharmaceutical carrier.

12. A method of restoring learning and treating memory difficulties which comprises administering to a mammal in need thereof a non-toxic effective amount of a compound of Structure (1) of claim 1 or a pharmaceutically acceptable salt thereof.

* * * * *